(12) United States Patent
Lackenbauer

(10) Patent No.: US 8,739,350 B1
(45) Date of Patent: Jun. 3, 2014

(54) DENTAL IMPLANT POST CLEANER

(76) Inventor: Everett Lackenbauer, Central Islip, NY (US)

( * ) Notice: Subject to any disclaimer, the term of this patent is extended or adjusted under 35 U.S.C. 154(b) by 0 days.

(21) Appl. No.: 13/397,165

(22) Filed: Feb. 15, 2012

(51) Int. Cl.
*A46B 5/02* (2006.01)
*A46B 9/04* (2006.01)
*B08B 9/00* (2006.01)

(52) U.S. Cl.
USPC ............ 15/160; 15/106; 15/104.01; 15/167.1

(58) Field of Classification Search
None
See application file for complete search history.

(56) References Cited

U.S. PATENT DOCUMENTS

| | | | |
|---|---|---|---|
| 887,181 A | 5/1908 | Barnes | |
| 1,897,365 A | 2/1933 | Duey | |
| 2,066,241 A | 12/1936 | Trattner et al. | |
| 3,088,150 A | 5/1963 | Sweeney | |
| 4,301,567 A | 11/1981 | Tucker | |
| 4,899,409 A | 2/1990 | Cox, Jr. | |
| 4,941,227 A | 7/1990 | Sussman | |
| 5,067,195 A | 11/1991 | Sussman | |
| 5,249,962 A | 10/1993 | Ascher | |
| 5,566,416 A * | 10/1996 | Karls | 15/104.04 |
| 5,940,923 A * | 8/1999 | Gunning | 15/106 |

* cited by examiner

*Primary Examiner* — Monica Carter
*Assistant Examiner* — Stephanie Berry
(74) *Attorney, Agent, or Firm* — Michael I. Kroll

(57) ABSTRACT

The present invention is a dental implant post cleaner, comprising a tubular housing having two open ends with an outer peripheral wall surface incorporating a frictional element and an inner peripheral wall surface with a plurality of interiorly extending bristles, for cleaning a dental implant post when inserted over and repetitiously manually rotated about the dental implant post. Furthermore, the tubular housing contains two oppositely beveled surfaces extending towards the inner peripheral wall surface forming two annular ridges, so that either one of the annular ridges will engage with a gum line about the dental implant post during a cleaning session. Also, a storage compartment in a holder being a handle of a toothbrush comprises a horizontal shaft for retaining the dental implant cleaning device therein when not in use.

10 Claims, 12 Drawing Sheets

DENTAL IMPLANT POST CLEANER

BACKGROUND OF THE INVENTION

1. Field of the Invention

The present invention relates generally to a dental hygiene device and, more specifically, to a dental implant post cleaner comprising a tubular housing having two open ends, with an outer peripheral wall surface and an inner peripheral wall surface with a plurality of interiorly extending bristles for cleaning a dental implant post when encompassed by the tubular housing and repetitiously manually rotated about the dental implant post. The tubular housing can also contain on the outer peripheral wall surface a texture, ridges or grooves to aid in gripping the tubular housing during use.

Furthermore, the tubular housing contains two opposite beveled surfaces extending towards the inner peripheral wall surface and having two annular ridges, so that either one of the annular ridges will engage with a gum line about the dental implant post during a cleaning session.

Still further, the tubular housing can have a longitudinal slot extending along its entire length, thereby enabling a diametric expansion or compression of the tubular housing when fitted over the dental implant post to accommodate dental implant posts of varying cross sectional sizes.

Also, a holder being a storage compartment in a handle of a toothbrush comprises a horizontal shaft therein for holding the dental implant cleaning device to create and enhance dental cleaning care kit.

A flange is formed on a distal end of the horizontal shaft, so that when the tubular housing is placed onto the horizontal shaft the flange prevents the tubular housing from sliding off of the horizontal shaft.

2. Description of the Prior Art

There are other devices designed for cleaning various items. Typical of these is U.S. Pat. No. 887,181 issued to Barnes on May 12, 1908.

Another patent was issued to Duey on Feb. 14, 1933 as U.S. Pat. No. 1,897,365. Yet another U.S. Pat. No. 2,066,241 was issued to Trattner et al. on Dec. 29, 1936 and still yet another was issued on May 7, 1963 to Sweeney as U.S. Pat. No. 3,088,150.

Another patent was issued to Tucker on Nov. 24, 1981 as U.S. Pat. No. 4,301,567. Yet another U.S. Pat. No. 4,899,409 was issued to Cox, Jr. on Feb. 13, 1990. Another was issued to Sussman on Jul. 17, 1990 as U.S. Pat. No. 4,941,227 and still yet another was issued on Nov. 26, 1991 to Sussman as U.S. Pat. No. 5,067,195.

Another patent was issued to Ascher on Oct. 5, 1993 as U.S. Pat. No. 5,249,962. Yet another U.S. Pat. No. 5,566,416 was issued to Karis on Oct. 22, 1996. Another was issued to Gunning on Aug. 24, 1999 as U.S. Pat. No. 5,940,923.

A brush of the character described comprising a substantially U-shaped back of a size sufficient to encompass the teeth, said U-shaped back being provided on the inner surface thereof with the suitable bristles or brush material, the bristles under the upper portion of the back diminishing in length from the outer to the inner edge of the back and the bristles on the lower portions of the back increasing in length toward the lower ends of the back, substantially as described A toothbrush comprising a handle formed with a tapered socket at one end thereof, a brush head including bristles disposed to impart to the brush end an annular formation, and a tapered stem on said brush head having a reduced outer end portion for insertion longitudinally into said socket; and effect wedge engagement between the stem and brush handle.

A toothbrush comprising an inverted substantially U-shaped body having substantially converging arms, bristles extending at an upward angle from the confronting face of the arms, bristles extending from the intermediate of the body toward the first mentioned bristles, and a handle extending from one of the arms and on the outer face thereof opposed to its bristles, and said handle adapted to be rocked in a vertical plane to cause like movement of the bristles with respect to the teeth.

A cleaning device comprising a hollow cylindrical base member opened at both ends, said member including a radially inwardly extending annular flange means at one end thereof and internal threads adjacent the other end thereof; an annular brushing element removably arranged in said base member in concentric relation therewith with its bristles extending inwardly; a brush holder having external threads thereon removably threadedly engaged to said internal threads of said base member and coacting with said flange means to retain said brushing element in said base member; an elongated hollow cover of sufficient length to be manually grasped and thereby operative to shield another brush carried by said brush holder within its hollow interior when so grasped, said cover including external threads formed at said open end thereof and being removably threadedly engaged to said internal threads of said base member and outwardly of said brush holder, whereby said annular brush is operative for cleaning battery terminals and the like when the elongated is manually grasped, and said annular brushing element can be replaced by removing said elongated cover and said brush holder from said base member.

A rotary terminal cleaner for cleaning terminals such as on automotive batteries and the like includes a cylindrical housing having an internal key running along the housing, an end cap having a cylindrical shape for mating with the hollow housing and forming a snug fit within an end of the hollow housing, the end cap having a longitudinal slot to mate with the key of the housing to prevent relative rotation of the end cap and the housing, the end cap also having a shaft integrally formed with the end cap for driving the cleaner by a rotary device such as a power drill. The cleaner also includes first and second brushes of abrasive material which fit within the hollow housing to abrade and clean the terminals. The first brush is a rectangular piece of abrasive material perhaps having bristles such as a section of a wire brush which fits in the end cap in such a manner as to permit the bristles to be facing the open end of the hollow housing. The second brush is a strip having a generally rectangular shape also having a plurality of bristles the second brush being formed in a circular manner within the hollow housing in such a manner as to be held in place by the key way on the inside of the housing and which in turn holds the first brush in fixed position.

A manual tool for preparing tube ends and/or pipe ends for jointure is provided, to perform the functions of scraping for cleaning, scarifying, deburring and abrading to remove grit and foreign matter such as solder, solder drops, chemical substances, or other debris on the outer and/or inner surfaces of the ends of tubing, pipe fittings and the like, prior to connection of said tubing, pipe and fittings by welding, soldering, etc. A plurality of tool units are detachably connected to a manual tool comprising a tool body adapted to fit readily and comfortably in the hand of a user, said tool body having a generally circular shape. The tool units may comprise: external brush units, internal brush units, external sharpened blade units, internal metal blades or ribs having sharpened edges and the like or other desirable tool units having sharpened edges, abrasive surfaces, and the like to perform the desired cleaning, scarifying, scraping, etc. necessary to provide cleaned tubing ends, piping ends, and the like to allow better connection of said tubing ends, piping ends, etc.

A device for cleaning dental implant posts, includes a handle for grasping the device; and a brush secured to one end of the handle. The brush includes (i) a first flexible, springy resilient wire or plastic member secured to the one end of the handle and having a substantially part-circular configuration extending over an arc greater than 90.degree. and less than 180.degree., the first member having a first inturned free end, (ii) a second flexible, springy resilient wire or plastic member secured to the same end of the handle and having a substantially part-circular configuration extending over an arc greater than 90.degree. and less than 180.degree., the second member having a second inturned free end in opposing and at least partially facing relation to the first inturned free end so as to define a gap between the first and second inturned free ends which is smaller than the distance between proximal and distal sides of an implant post to be cleaned; and (iii) a plurality of circumferentially arranged bristles secured to each wire or plastic member. The first and second members may be made as a single unitary wire member.

A device for cleaning dental implant posts, includes a handle for grasping the device; and a brush secured to one end of the handle. The brush includes (i) a first flexible, springy resilient wire or plastic member secured to the one end of the handle and having a substantially part-circular configuration extending over an arc greater than 90.degree. and less than 180.degree., the first member having a first inturned free end, (ii) a second flexible, springy resilient wire or plastic member secured to the same end of the handle and having a substantially part-circular configuration extending over an arc greater than 90.degree. and less than 180.degree., the second member having a second inturned free end in opposing and at least partially facing relation to the first inturned free end so as to define a gap between the first and second inturned free ends which is smaller than the distance between proximal and distal sides of an implant post to be cleaned; and (iii) a plurality of circumferentially arranged bristles secured to each wire or plastic member. The first and second members may be made as a single unitary wire member.

A method and device for cleaning abutment members of a dental implant in which a relatively rigid support member carries a cleaning element into a position around the lingual surface of the abutment member to be cleaned whereafter the cleaning element can be rubbed against the abutment member to effect the cleaning. The cleaning element can be fixed to the support member in which case, the support member is manipulated to achieve the cleaning of the abutment member by the cleaning element. Alternatively, the support member can be removed from the mouth after the cleaning element has been put into place around the abutment member whereafter cleaning of the abutment member is achieved by the cleaning element itself.

A two-in-one brush for an item to be cleaned comprises a hollow, generally cylindrical, one-piece handle having a pair of open end portions, a grippable external surface and a transverse web disposed perpendicular to the handle between the open end portions. An annular female brush member is fixed within one open end portion of the handle and a male brush member is anchored within the other open end portion. The brush members have outermost ends terminating within the open end portions and being continuously accessible therefrom wherein the handle substantially shields the brush members from inadvertent manual contact therewith yet permits contact of the brush members with the item to be cleaned.

The present invention provides an improved device for cleaning dental implant posts comprising a handle specifically adapted for ease of use by a person of limited or impaired dexterity or muscle control or a care giver and a series of brush and pick attachments specifically adapted for cleaning dental implant posts. This handle configuration eliminates the need for a pencil-like grip.

While these cleaning devices may be suitable for the purposes for which they were designed, they would not be as suitable for the purposes of the present invention, as hereinafter described.

SUMMARY OF THE PRESENT INVENTION

A primary object of the present invention is to provide a dental implant cleaning device that is capable of cleaning the interface area between a dental implant post and the gum line area of a user.

Another object of the present invention is to provide a dental implant cleaning device comprising a tubular housing having an outer peripheral wall surface and an inner peripheral wall surface extending from two open ends.

Yet another object of the present invention is to provide a dental implant cleaning device wherein the tubular housing can be manufactured from either a rigid material or from a malleable material.

Still yet another object of the present invention is to provide an outer peripheral wall surface of the tubular housing having a texture, ridges or grooves to aid in gripping the tubular housing during use.

An additional object of the present invention is to provide a dental implant cleaning device wherein the tubular housing contains on each of the two opposite open ends a beveled surface extending towards the inner peripheral wall surface and an annular ridge, so that either one of the annular ridges can contact the gum line about the dental implant post.

A further object of the present invention is to provide a dental implant cleaning device in which the inner peripheral wall surface of the tubular housing has a plurality of bristles extending radially therein for cleaning the dental implant post.

A yet further object of the present invention is to provide a dental implant cleaning device, wherein the plurality of bristles extend between the annular ridges of the tubular housing, so that the bristles can project beyond the annular ridges to more easily clean the gum line about the dental implant post.

A still yet further object of the present invention is to provide a dental implant cleaning device having a longitudinal slot extending the length of the tubular housing, thereby enabling a diametric expansion or compression of the tubular housing during a cleaning task to accommodate dental implant posts of varying cross sectional sizes.

Another object of the present invention is to provide a dental implant cleaning device utilizing a holder having a storage compartment formed therein, wherein the storage compartment contains a horizontal shaft for retaining the tubular housing between cleaning sessions.

Yet another object of the present invention is to provide a dental implant cleaning device wherein the holder is located within a handle of a toothbrush, thereby creating a dental hygiene cleaning kit, where permanent teeth or dentures can be brushed clean by the toothbrush, while the dental implant post can be cleaned with the dental implant cleaning device.

Still yet another object of the present invention is to provide a dental implant cleaning device wherein the horizontal shaft incorporates a flange on a distal end, so that the tubular housing of the dental implant cleaning device can be mounted onto the horizontal shaft, whereby the bristles will not be deformed during storage.

Additional objects of the present invention will appear as the description proceeds.

The present invention overcomes the shortcomings of the prior art by providing a dental implant post cleaner, comprising a tubular housing having two open ends with an outer peripheral wall surface incorporating a frictional element and an inner peripheral wall surface with a plurality of interiorly extending bristles, for cleaning a dental implant post when inserted over and repetitiously manually rotated about the dental implant post. Furthermore, the tubular housing contains two oppositely beveled surfaces extending towards the inner peripheral wall surface forming two annular ridges, so that either one of the annular ridges will engage with a gum line about the dental implant post during a cleaning session. Also, a storage compartment in a holder being a handle of a toothbrush comprises a horizontal shaft for retaining the dental implant cleaning device therein when not in use.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
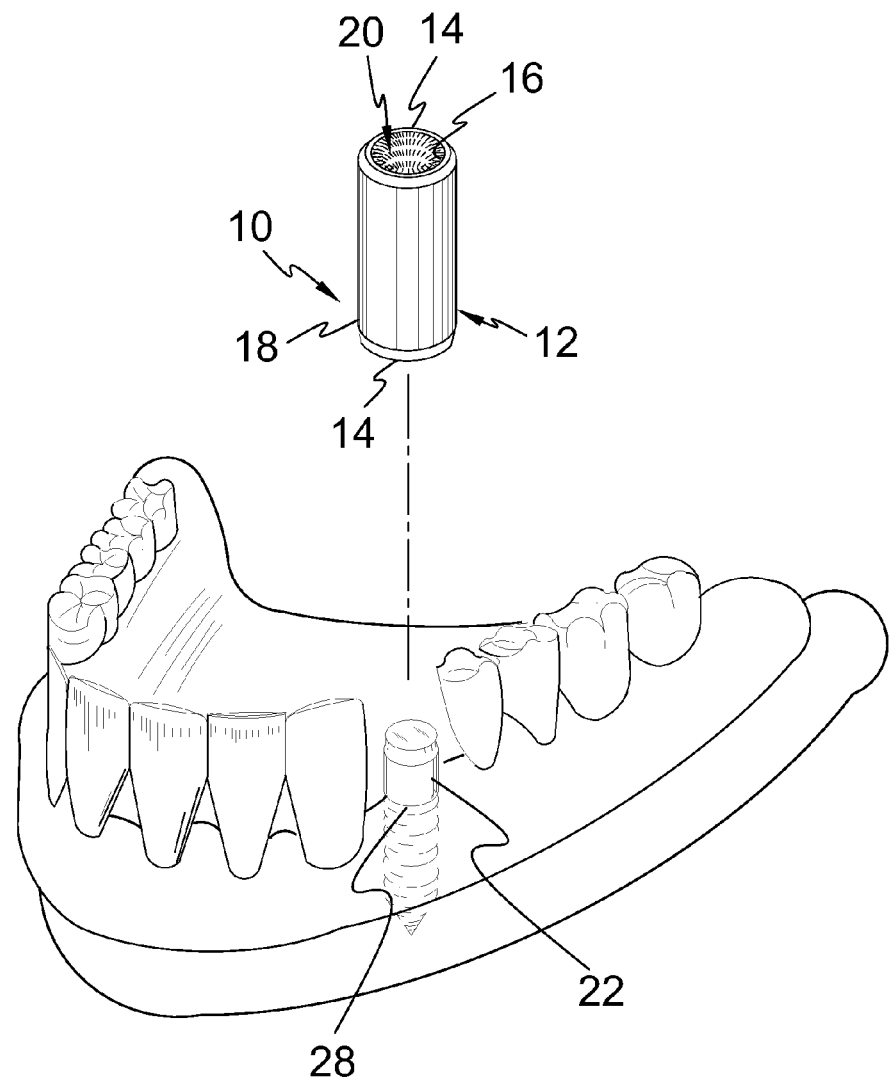
FIG. 1 is a perspective view of the present invention exploded from a dental implant post.

Turning now descriptively to the drawings, in which similar reference characters denote similar elements throughout the several views, the Figures illustrate the dental implant post cleaner of the present invention. With regard to the reference numerals used, the following numbering is used throughout the various drawing figures.

10 dental implant post cleaner
12 tubular housing of cleaner 10
14 open end of tubular housing 12
16 inner peripheral wall surface of tubular housing 12
18 outer peripheral wall surface of tubular housing 12
20 cleaning components of cleaner 10
22 dental implant post
24 beveled surface at open end 14
26 annular ridge at beveled surface 24
28 gum line
30 bristles for cleaning components 20
32 texture on tubular housing 12
34 ridges on tubular housing 12
36 grooves on tubular housing 12
38 ridged material of tubular housing 12
40 malleable material of tubular housing 12
42 longitudinal slot in tubular housing 12
44 holder
46 open ended storage compartment of holder 44
48 horizontal shaft of holder 44
50 flange on horizontal flange 48
52 handle of toothbrush 54
54 toothbrush

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

Referring to FIG. 1, shown is a perspective view of the present invention exploded from a dental implant post.

Figure 2:
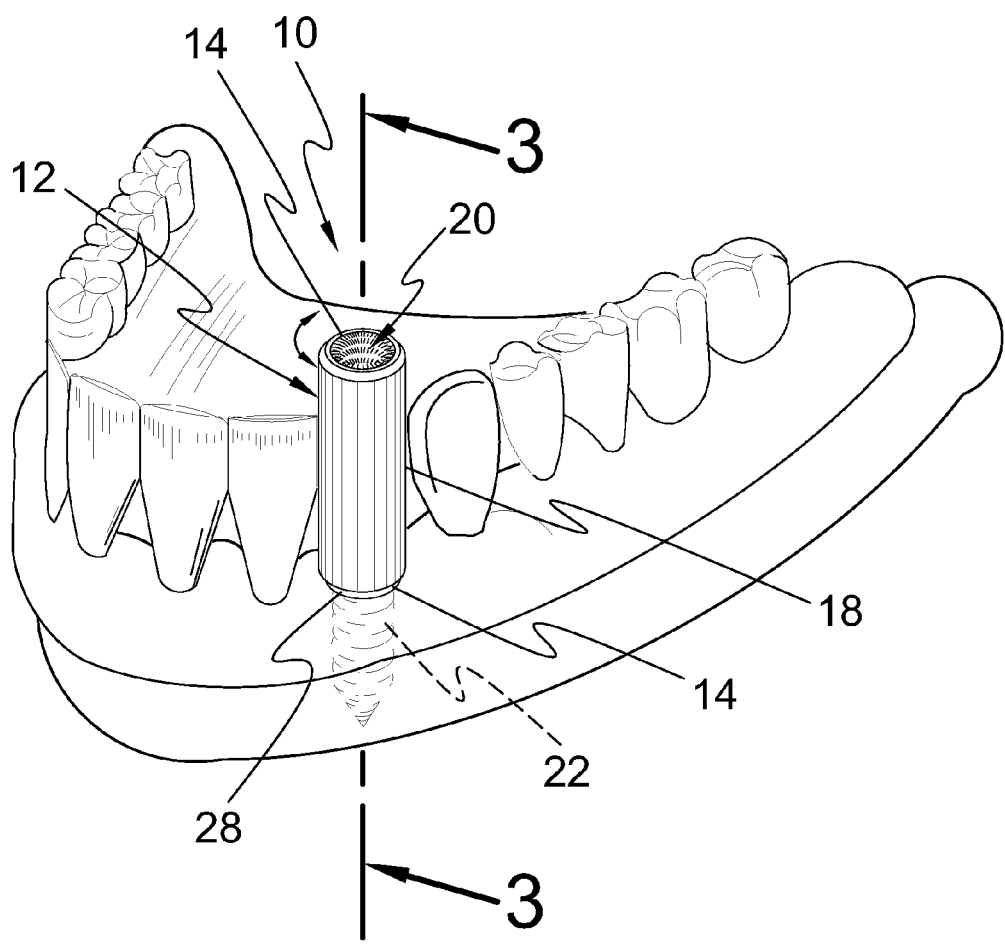
FIG. 2 is a perspective view of the present invention inserted onto the dental implant post.

Referring to FIG. 2, shown is a perspective view of the present invention inserted onto the dental implant post.

Figure 3:
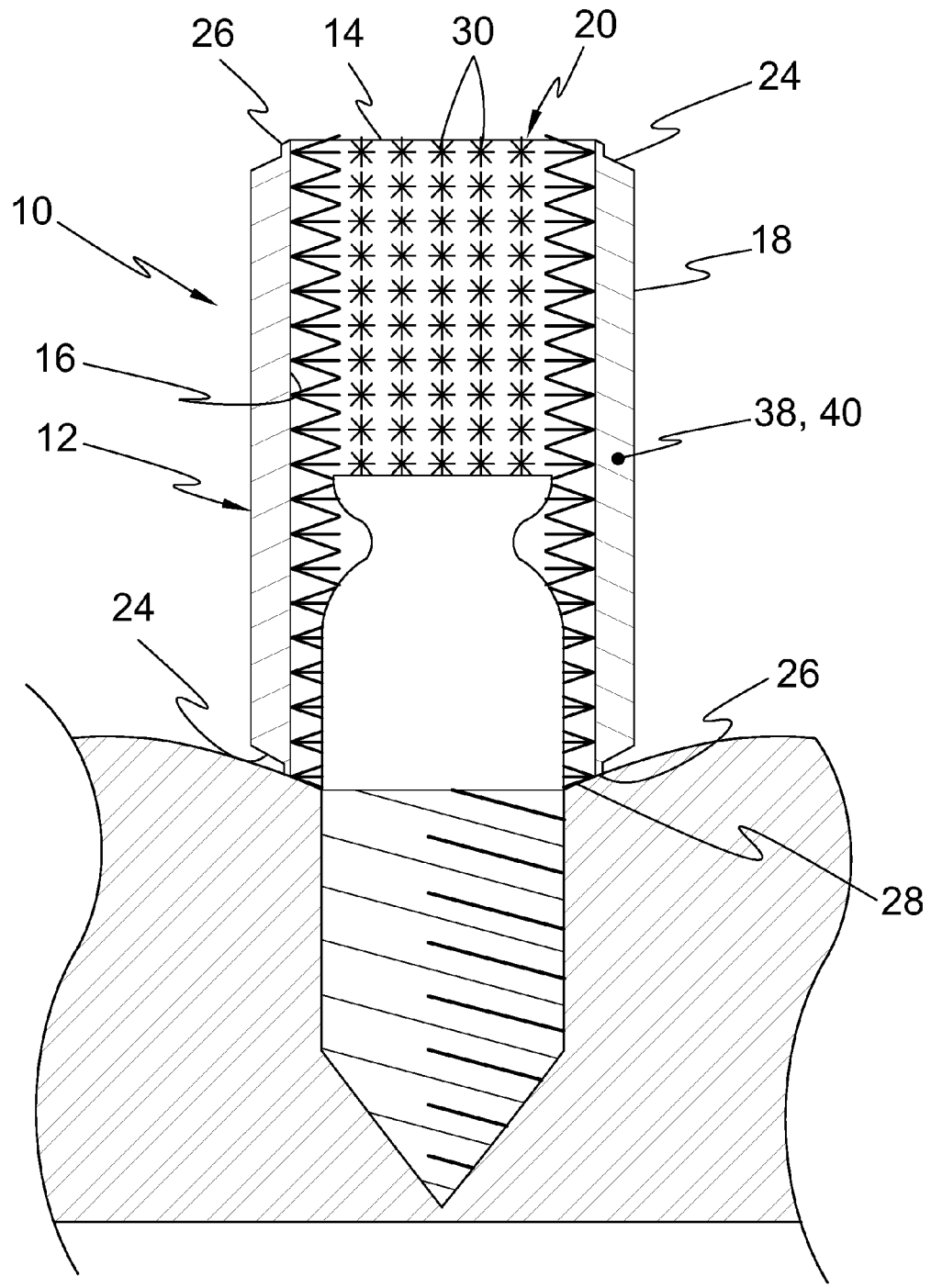
FIG. 3 is a cross sectional view taken along line 3-3 in FIG. 2.

Referring to FIG. 3, shown is a cross sectional view taken along line 3-3 in FIG. 2. The present invention is a dental implant post cleaner 10 which comprises a tubular housing 12 having two open ends 14, with an inner peripheral wall surface 16 and an outer peripheral wall surface 18. Components 20 on the inner peripheral wall surface 16 are for cleaning a dental implant post 22, when either one of the open ends 14 of the tubular housing 12 is inserted over the dental implant post 22 and the tubular housing 12 is repetitiously manually rotated about the dental implant post 22.

Figure 4:
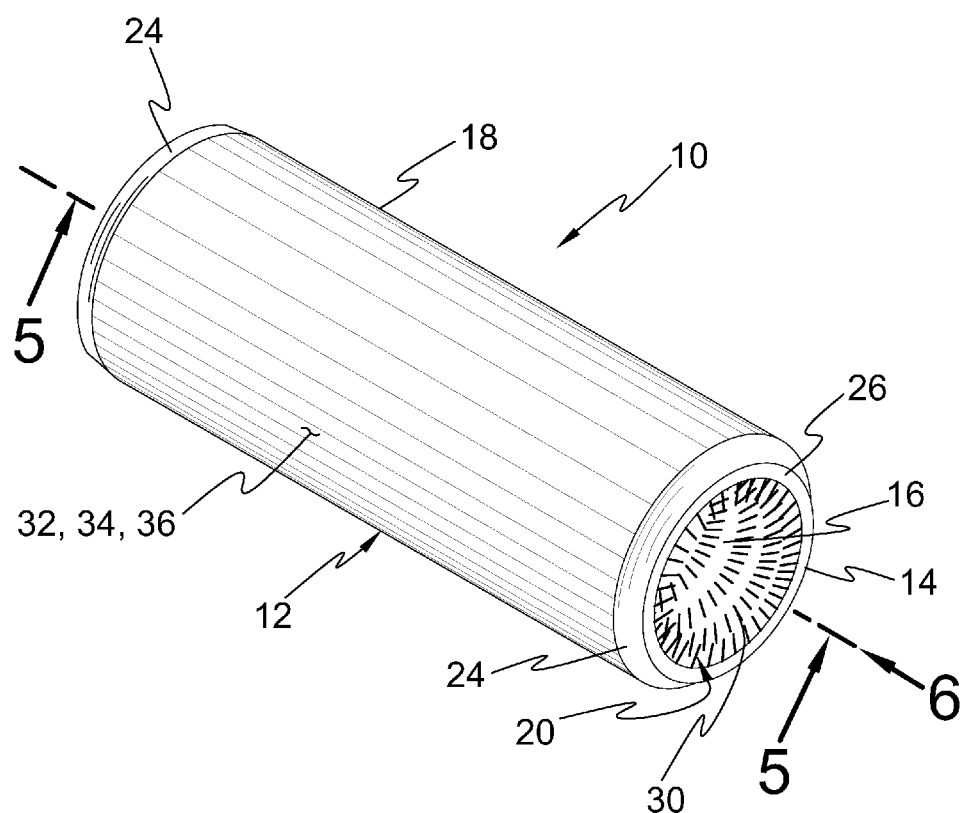
FIG. 4 is a perspective view of the present invention per se.

Referring to FIG. 4, shown is a perspective view of the present invention per se.

Figure 5:
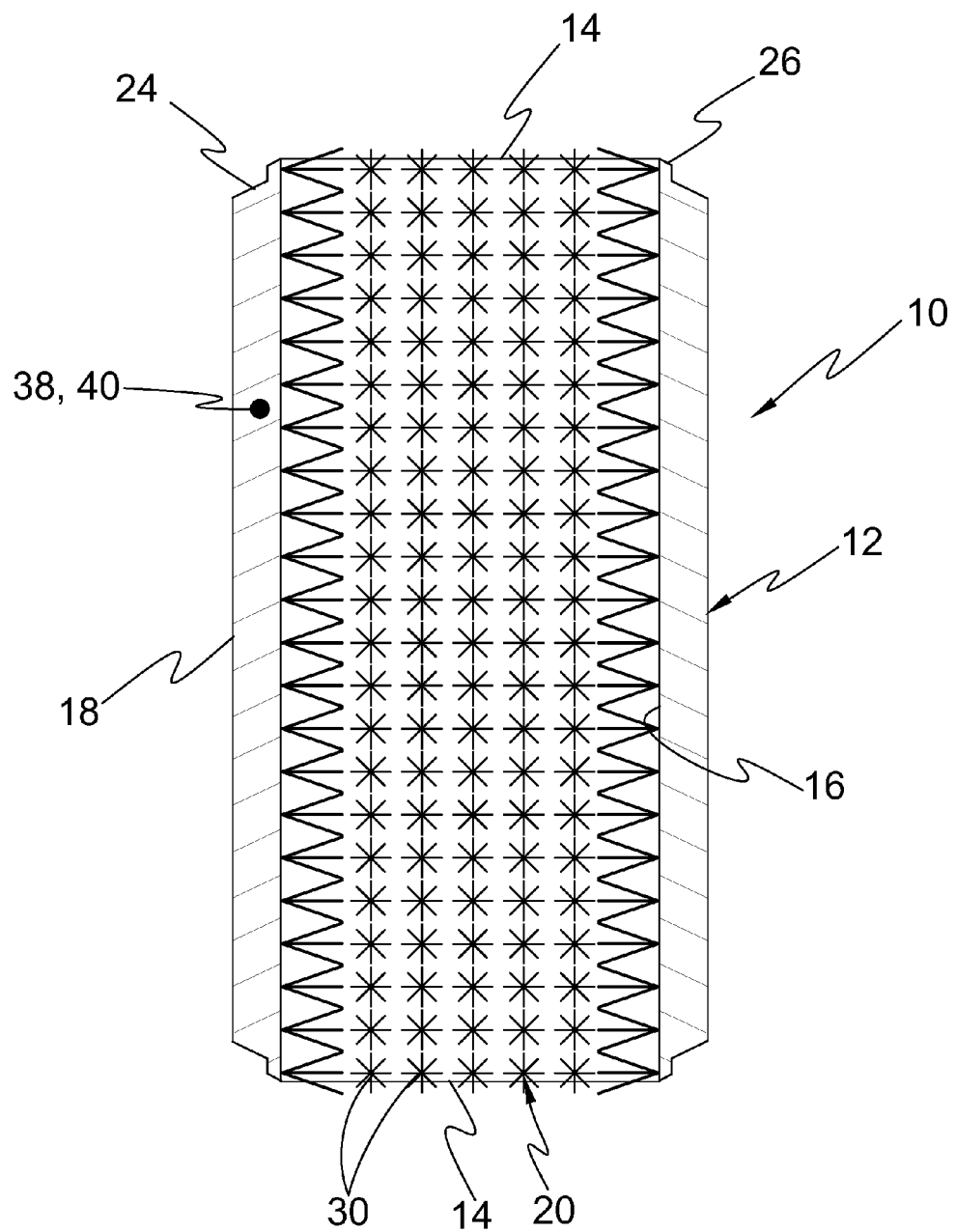
FIG. 5 is a cross sectional view of the present invention taken along line 5-5 in FIG. 4.

Referring to FIG. 5, shown is a cross sectional view of the present invention taken along line 5-5 in FIG. 4.

Figure 6:
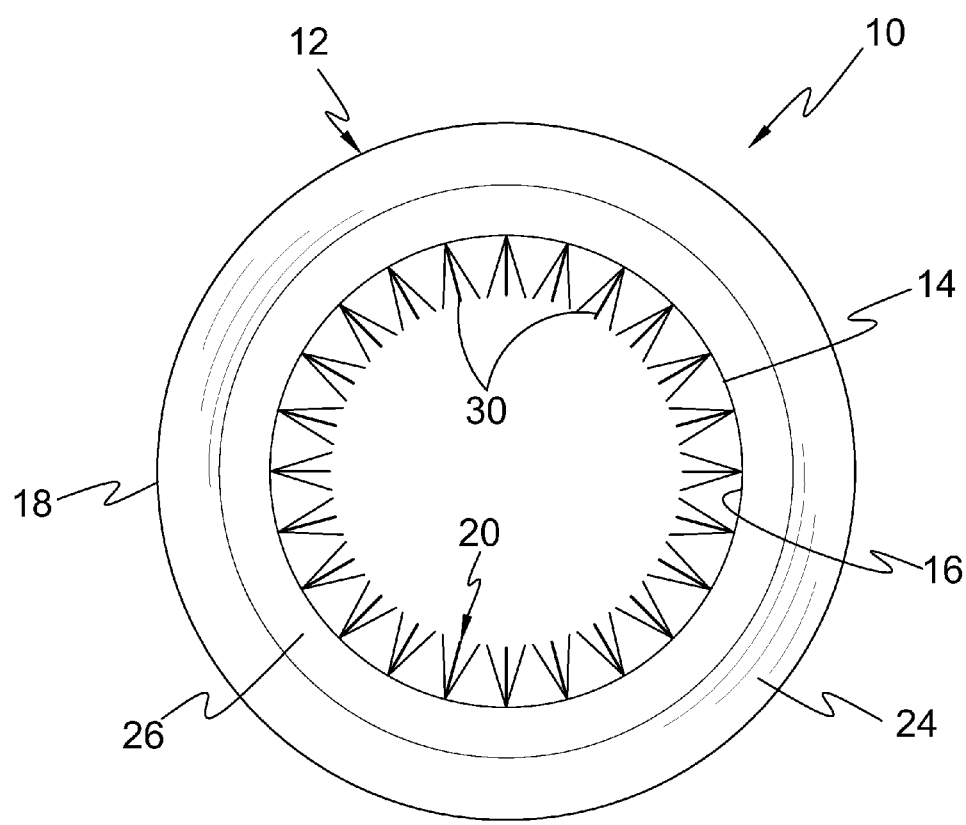
FIG. 6 is an end view taken in the direction of arrow 6 in FIG. 4.

Referring to FIG. 6, shown is an end view taken in the direction of arrow 6 in FIG. 4. Each open end 14 of the tubular housing 12 comprises a beveled surface extending towards the inner peripheral wall surface 16. An annular ridge 26 is located between the beveled surface 24 and the inner peripheral wall surface 16, so that the annular ridge 26 will engage with a gum line 28 about the dental implant post 22, when the dental implant post is being cleaned.

The cleaning components 20 comprises a plurality of interiorly extending bristles 30 affixed to the inner peripheral wall surface 16 between the two opposite annular ridges 26, so that the bristles 30 can project beyond the two opposite annular ridges 26 to more easily clean the gum line 28 about the dental implant post 22.

The outer peripheral wall surface 18 of the tubular housing comprises a texture 32 to aid in gripping the tubular housing 12. The outer peripheral wall surface 18 of the tubular housing 12 can also comprise ridges 34 to aid in gripping the tubular housing 12. The outer peripheral wall surface 18 of the tubular housing 12 can also comprise grooves 36 to aid in gripping the tubular housing 12. The tubular housing 12 can be manufactured from a ridged material 38. The tubular housing 12 can also be manufactured from a malleable material 40.

Figure 7:
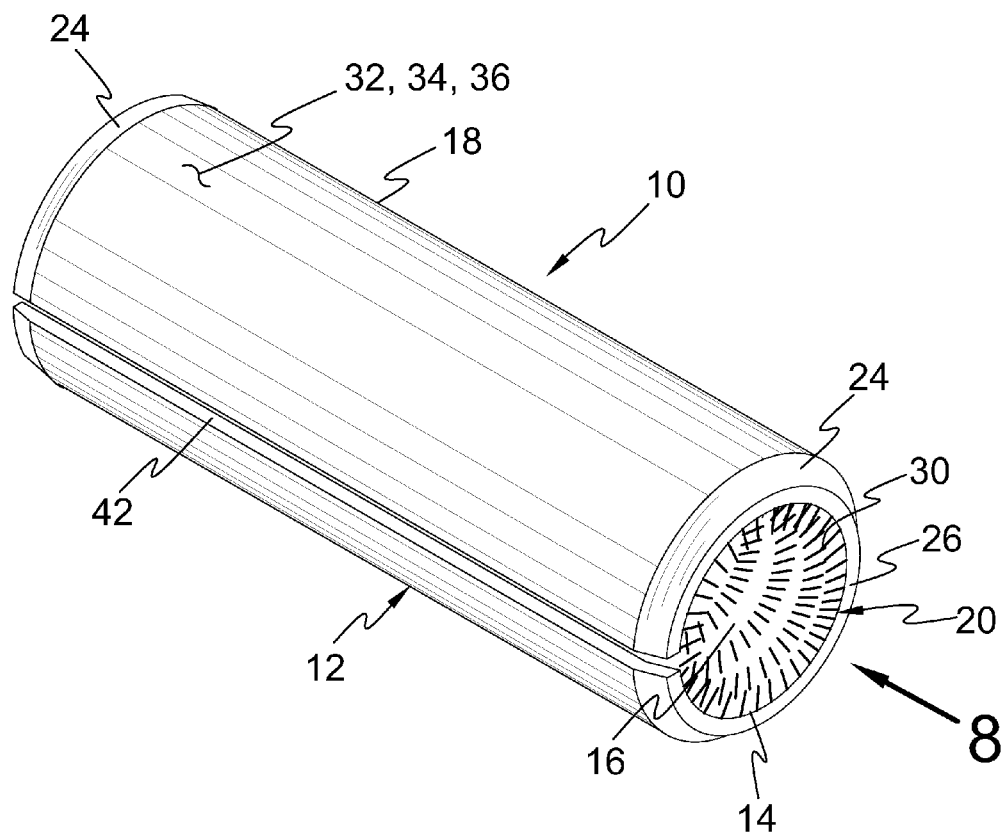
FIG. 7 is a perspective view, similar to FIG. 4, having a longitudinal slot therealong.

Referring to FIG. 7, shown is a perspective view, similar to FIG. 4, having a longitudinal slot therealong.

Figure 8:
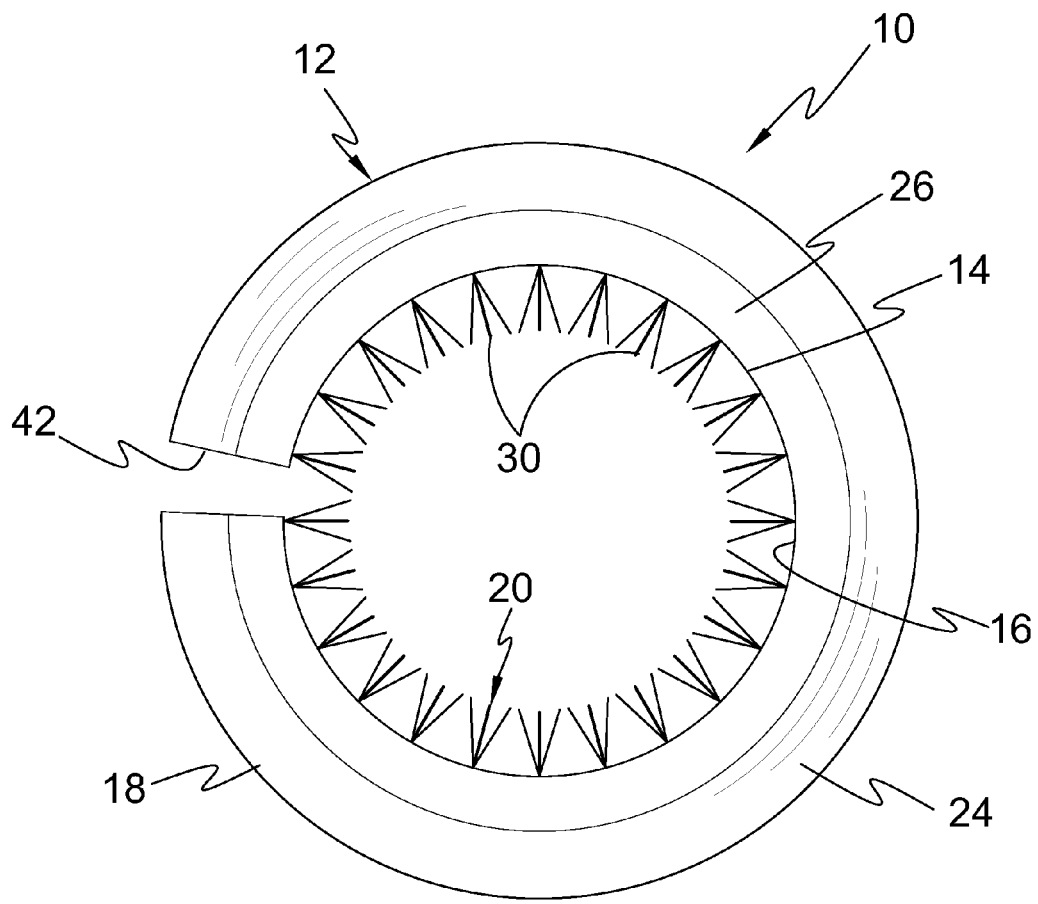
FIG. 8 is an end view taken in the direction of arrow 8 in FIG. 7.

Referring to FIG. 8, shown is an end view taken in the direction of arrow 8 in FIG. 7. The tubular housing 12 can also have a longitudinal slot 42 extending along its entire length, whereby enabling a diametric expansion and compression of the tubular housing 12 during a cleaning task to accommodate dental implant posts 22 of varying cross sectional sizes.

Figure 9:
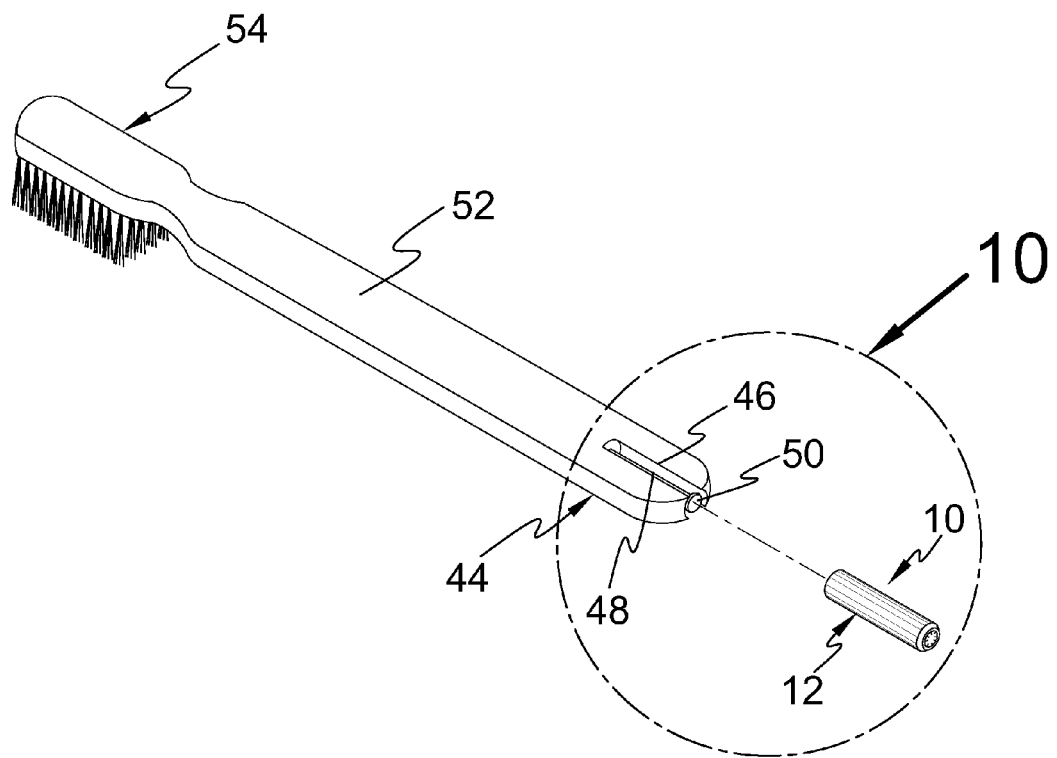
FIG. 9 is a perspective view of a toothbrush with a handle being a holder having a storage compartment built therein for retaining the implant cleaning device when not in use, but exploded therefrom.

Referring to FIG. 9, shown is a perspective view of a toothbrush with a handle being a holder having a storage compartment built therein for retaining the implant cleaning device when not in use, but exploded therefrom.

Figure 10:
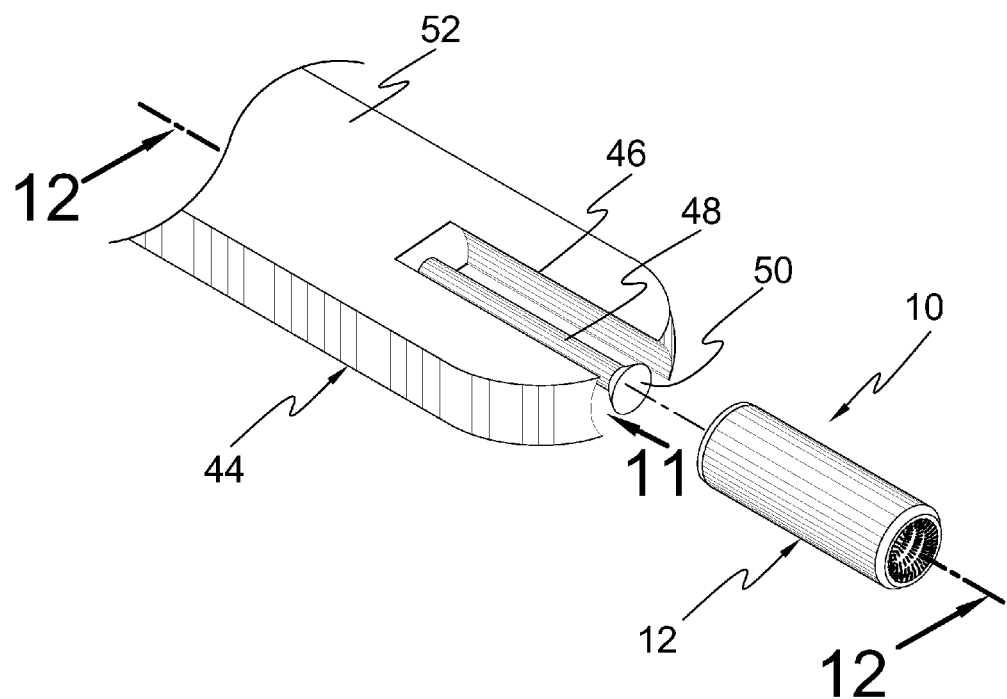
FIG. 10 is an enlarged perspective view of the area indicated by arrow 10 in FIG. 9.

Referring to FIG. 10, shown is an enlarged perspective view of the area indicated by arrow 10 in FIG. 9.

Figure 11:
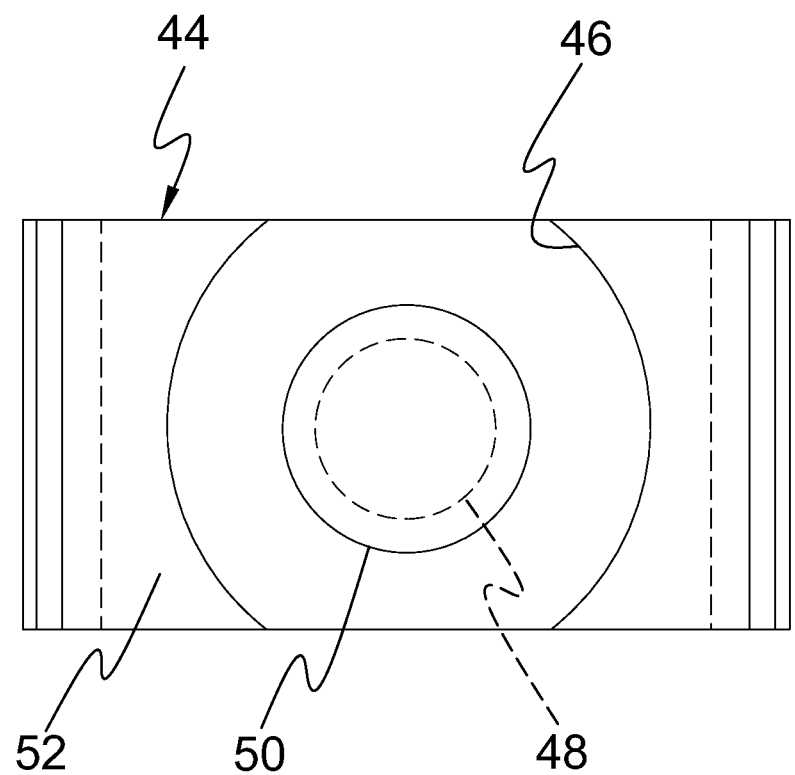
FIG. 11 is a rear view taken in the direction of arrow 11 in FIG. 10.

Referring to FIG. 11, shown is a rear view taken in the direction of arrow 11 in FIG. 10.

Figure 12:
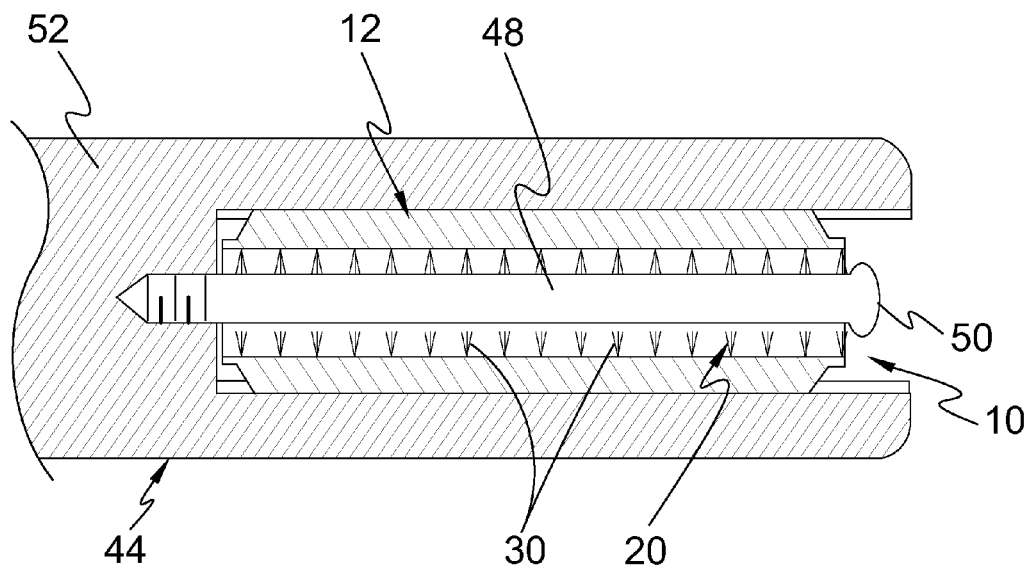
FIG. 12 is a cross sectional view taken along line 12-12 in FIG. 11, with the present invention installed within the storage compartment.

Referring to FIG. 12, shown is a cross sectional view taken along line 12-12 in FIG. 11, with the present invention installed within the storage compartment. The dental implant post cleaner 10, further comprises a holder 44 having an open ended storage compartment 46 to removably retain the tubular housing 12 therein between cleaning sessions. The holder 44 further comprises a horizontal shaft 48 affixed within the open ended storage compartment 46, whereby the tubular housing 12 can be mounted onto the horizontal shaft 48.

The horizontal shaft 48 comprises a flange 50 formed about a distal end, so that when the tubular housing 12 is mounted onto the horizontal shaft 48 the bristles 30 will not be deformed during storage. The holder 44 is comprised within a handle 52 of a toothbrush 54, thereby creating a dental hygiene cleaning kit, wherein permanent teeth and dentures can be brushed clean by the toothbrush 54, while the dental implant post 22 can be cleaned by the bristles 30 located within the tubular housing 12.

What is claimed is:

1. A dental implant post cleaner which comprises:

a) a tubular housing having two open ends, with an inner peripheral wall surface and an outer peripheral wall surface;
b) each open end of the tubular housing comprises a beveled surface extending towards the inner peripheral wall surface and an annular ridge located between the beveled surface and the inner peripheral wall surface;
c) means, on the inner peripheral wall surface, for cleaning a dental implant post comprising a plurality of interiorly extending bristles affixed to the inner peripheral wall surface between the two opposite annular ridges, so that the bristles can project beyond the two opposite annular ridges to more easily clean the gum line about the dental implant post, when either one of the open ends of the tubular housing is inserted over the dental implant post and the tubular housing is repetitiously manually rotated about the dental implant post, and whereby the annular ridge will engage with a gum line about the dental implant post when the dental implant post is being cleaned; and
d) a holder having an open ended storage compartment to removably retain the tubular housing therein between cleaning sessions.

2. The dental implant post cleaner as recited in claim 1, wherein the outer peripheral wall surface of the tubular housing comprises a texture to aid in gripping the tubular housing.

3. The dental implant post cleaner as recited in claim 1, wherein the outer peripheral wall surface of the tubular housing comprises ridges to aid in gripping the tubular housing.

4. The dental implant post cleaner as recited in claim 1, wherein the outer peripheral wall surface of the tubular housing comprises grooves to aid in gripping the tubular housing.

5. The dental implant post cleaner as recited in claim 1, wherein the tubular housing is manufactured from a ridged material.

6. The dental implant post cleaner as recited in claim 1, wherein the tubular housing is manufactured from a malleable material.

7. The dental implant post cleaner as recited in claim 1, wherein the tubular housing further having a longitudinal slot extending along its entire length, whereby enabling a diametric expansion and compression of the tubular housing during a cleaning task to accommodate dental implant posts of varying cross sectional sizes.

8. The dental implant post cleaner as recited in claim 1, wherein the holder further comprises a horizontal shaft affixed within the open ended storage compartment, whereby the tubular housing can be mounted onto the horizontal shaft.

9. The dental implant post cleaner as recited in claim 8, wherein the horizontal shaft comprises a flange formed about a distal end, so that when the tubular housing is mounted onto the horizontal shaft the bristles will not be deformed during storage.

10. The dental implant post cleaner as recited in claim 9, wherein the holder is comprised within a handle of a toothbrush, thereby creating a dental hygiene cleaning kit, wherein permanent teeth and dentures can be brushed clean by the toothbrush, while the dental implant post can be cleaned by the bristles located within the tubular housing.

* * * * *